United States Patent [19]
Smith et al.

[11] Patent Number: 5,503,975
[45] Date of Patent: Apr. 2, 1996

[54] MECHANISM BASED INHIBITORS OF DNA METHYLTRANSFERASE

[75] Inventors: Steven S. Smith, Los Angeles; Bruce E. Kaplan, Claremont, both of Calif.

[73] Assignee: City of Hope, Duarte, Calif.

[21] Appl. No.: 861,899
[22] PCT Filed: Oct. 21, 1991
[86] PCT No.: PCT/US91/07622
  § 371 Date: Jun. 22, 1992
  § 102(e) Date: Jun. 22, 1992
[87] PCT Pub. No.: WO92/06985
  PCT Pub. Date: Apr. 30, 1992

Related U.S. Application Data

[63] Continuation-in-part of Ser. No. 598,665, Oct. 23, 1990, which is a continuation of Ser. No. 317,670, Mar. 1, 1989, abandoned.

[51] Int. Cl.⁶ .................. C12Q 1/68; C12Q 1/00
[52] U.S. Cl. ................................ 435/6; 435/15
[58] Field of Search ............... 536/22.1, 25.3; 514/45, 46, 49, 50; 435/15, 6

[56] References Cited

FOREIGN PATENT DOCUMENTS 900907  9/1990  WIPO .

OTHER PUBLICATIONS

Websters Dictionary II, Riverside Publ. Co. (1984) p. 589.
Jones et al., Cell 20:85–93 (1980) "Cellular Differentiation, cytidine analogs . . .".
Osterman et al., Biochemistry 27:5204–5210 (1988) "5–fluorocytosine in DNA is a mehanism–based . . .".
Jones, Cancer Res. 46:461–466 (1986) "DNA Methylation and Cancer".
Lewis, Science 237:1570 (1987) "What does homology mean . . .".
Call, et al., "Studies of mutagenicity and clastogenicity of 5–azacytidine in human lyphoblasts and *Salmonella typhimurium*" *Mutation Research* 160:249–257 (1986).
Kaysen, et al., "Incorporation of 5–Fluorodeoxycytidine and Metabolites into Nucleic Acids of Human MCF–7 Breast Carcinoma Cells", *Cancer Research* 46:4534–4538 (1986).
Carr, et al., "The tumorigenicity of 5–azacytidine in the male Fischer rat", *Carcinogenesis* 5:158301590 (1984).
Hori, T. A. "Induction of chromosome decondensation, siter–chromatid exchanges and endoreduplications by 5–azacytidine, an inhibitor of DNA methylation", *Mutation Research* 121:47–52 (1983).
Schmid, et al., "A direct demonstration of somatically paired heterochromatin of human chromosomes", *Cytogenet. Cell Genet.* 36:554–561 (1983).

Primary Examiner—W. Gary Jones
Assistant Examiner—Eggerton Campbell
Attorney, Agent, or Firm—Edward S. Irons

[57] ABSTRACT

Novel synthetic oligomers of unique three-dimensional structure comprising homologous and heterologous blocks, some of which may self-associate are described. Also disclosed is a synthetic oligonucleotide that includes 5-fluorocytosine residues at positions corresponding to methylation sites of DNA-cytosine methyltransferase and a method for preparing such a molecule.

3 Claims, 10 Drawing Sheets

MECHANISM BASED INHIBITORS OF DNA METHYLTRANSFERASE

This invention was made with government support under Grant No. GM 38350 awarded by the National Institutes of Health. The government has certain rights in the invention.

This application is a continuation-in-part of U.S. application Ser. No. 598,665 filed 23 Oct., 1990, which is a continuation of U.S. application Ser. No. 317,670 filed 1 Mar. 1989 abandoned.

FIELD OF INVENTION

This invention relates to synthetic oligomers of unique three-dimensional structure that combine the principles of polymer, peptide and synthetic DNA chemistry to provide rationally designed drugs, drug delivery systems, research tools and other products.

The invention also relates to unique oligonucleotide molecules in which 5-fluorodeoxycytidine inhibits DNA methyltrnasferase.

BACKGROUND OF THE INVENTION

Various heteropolymers are known (see, e.g., Seela, F. and Kaiser, K., Oligodeoxyribonucleotides containing 1,3-propanediol as a nucleoside substitute, *Nucleic Acids Res.* 15:3113–3129 (1987) and Connolly, B. A., The Synthesis of Oligonucleotides containing a primary amino group at the 5'-terminus, *Nucleic Acids Res.* 15:3131–3139 (1987)) and one example of a heterodimer exists. See Lemaitre, M., Bayard, B., and Leblue, B., Specific Antiviral Activity of a Poly(L-lysine)-Conjugated Oligodeoxyribonucleotide Sequence Complementary to Vesicular Stomatitis N Protein mRNA Initiation Site, *Proc. Nat. Acad. Sci. U.S.A.* 84:648–652 (1987). However, there is no known disclosure of molecules comprising linked heterologous blocks conforming to a predetermined or predictable three-dimensional structure.

Definitions

The following definitions apply to terms used in this specification and in the claims:

Block—An oligomer component of at least about 5 monomers, e.g., carbon atoms, amino acid residues or nucleotides which has an intrinsic tendency to self-associate inter se or with another block.

Unit—An oligomer component consisting of at least three blocks.

Oligomer—A molecule having from about 12 to about 150 monomers, e.g., carbon atoms, amino acid residues or nucleotides and comprising at least one unit.

Self-Association—The capability shared by two or more blocks to form a mutual linkage, e.g., the capability of homologous nucleic acid sequences to hybridize and of certain peptides to interact.

Homologous Block—One of a series of blocks where members of the series exhibit common properties, for example, one of a series of nucleic acid, peptide or organic polymer blocks. Organic polymer blocks may generally comprise straight or branched chain polyolefins such as polyethylene, polypropylene or polystyrene and other kinds of polymers which are not cross-linked.

Heterologous Block—One of a series of blocks whose members do not exhibit common properties.

Heterologous Block Oligomer (HBO)—An oligomer comprising at least one unit of the schematic formula $A_1$-B-$A_2$ in which the block B is heterologous with respect to at least one of the blocks $A_1$ and $A_2$ and is constrained into a generally looped configuration by the self-association energy of the blocks $A_1$ and $A_2$ or in which the blocks $A_1$ and $A_2$ are heterologous and are constrained into a spatially juxtaposed position by the internal self-association of the block B.

SUMMARY OF THE INVENTION

HBO's provide a broad spectrum of novel molecules. The new molecules may be predesigned to achieve objectives which have been realized, with some difficulty, if at all.

HBO detergents can be formed with self-associated DNA blocks joined by simple linker blocks. The properties of these detergent molecules can be exploited in several ways. Micelles formed primarily of the self-associated DNA blocks may permit the passage of any short, double-stranded DNA through the bloodstream. Antisense molecules and short duplex DNA's more intrinsically resistant to DNase could be delivered in this fashion. "Suicide" substrates of duplex DNAs can be constructed to target tissues and neoplastic or virus infected cells. The inclusion of a hydrophobic linker block in these HBOs facilitates diffusion or transport across cell membranes at the requisite site.

A variety of applications in protein purification, for example, hydrophobic interaction chromatography are apparent. More specifically the biospecificity of DNA sequences may combine with the capacity of the linker block to interact with such a chromatographic column.

Both 5-fluorodeoxycytidine (FdCyd) and 5-azacytidine (azaC) have been shown to inhibit methylation of DNA with resultant effects on gene expression and cell differentiation. See, e.g., Jones and Taylor, *Cell* 20:85–93 (1980) and Osterman et al., *Biochemistry* 27:5204–5210 (1988). Instability is a major difficulty with azaC which hydrolyzes readily. Incorporation into DNA appears to increase stability to some extent. However, isolation of intact azaC containing DNA is difficult. See, Santi et al., *Proc. Natl. Acad. Sci. USA* 91:6993–6997 (1984).

In contrast, FdCyd and DNA containing FdCyd are stable to chemical hydrolysis. FdCyd, however, is susceptible to enzymatic deamination to toxic 5-fluorodeoxyuridine metabolites. See, Newman et al., *Proc. Natl. Acad. Sci. USA* 79:6419–6423 (1982).

Attempts to prepare synthetic oligonucleotides which contain FdCyd in appropriate positions corresponding to the methylation sites of DNA-cytosine methyltransferase have failed. See, Osterman, et al., supra. Hence resort was had to an enzymatic synthesis of poly (FdC-dG). Ibid. Hardy et al, *Biochemical and Biophysical Research Communications*, 145, 146–152 (1987) describe M13 DNAs in which carbon-5 of each deoxycytidine residue in one chain is replaced by a bulky group. These DNAs are shown to be good substrates for human DNA (cytosine-5) methyltransferase. These substituted DNA's were prepared by using 5 MedCTP, 5 BrdCTP, 5 IdCTP and 5 FdCTP in place of dCTP during primer extension as described in Messing J., *Methods in Enzymology* 101:20–78 (1983).

This invention provides self-priming HBOs in which (1) the blocks $A_1$ and $A_2$ are homologous DNA sequences (2) the block designated $A_2$ contains fewer, e.g., at least 10 fewer bases, and preferably from about 10 to about 50 fewer bases, than the block designated $A_1$, and in which the block $A_2$ is a primer for the block A and may be extended, for example, by a DNA polymerase with a combination of dNTPs and FdCTP. Such an HBO is depicted, for example, by the molecules designated 48L-1, 48L-2 and 48L-3 in Table 1, infra. This invention further provides synthetic oligonucleotide molecules produced by the extension of such a self-priming HBO with a combination of dNTPs and FdCTP. Such molecules are mechanism based inhibitors of human DNA methyltransferase.

DESCRIPTION OF THE FIGURES

For example, in such an HBO, the $A_1$ and $A_2$ blocks may be self-associating oligonucleotides, peptides or the like and the linker block B provides a preselected property, e.g., hydrophobicity. Alternatively, the linker block B may be nucleic acid sequences when the $A_1$ and $A_2$ blocks are self-associating peptides.

FIG. 5 depicts the Methyl-Directed DNA Methyltransferase Reaction.

FIG. 5B: Restriction analysis of the enzymatically labelled product. Labelling pattern predicted for the product of the methyl-directed reaction is shown on the left. The position of the 5-methylcytosine residue introduced synthetically is indicated with an (m); the predicted position of the 5-methylcytosine generated enzymatically is indicated with an (*). Cleavage sites for the indicated restriction enzymes are depicted as gaps. the autoradiograph on the right shows the sizes of the labelled restriction fragments observed after enzymatic labelling with [$^3$H-methyl]AdoMet.

FIG. 6 depicts consequences of the Enzyme Mechanism.

FIG. 6A: Mechanism of Human DNA(cytosine-5) methyl-transferases: Nucleophilic attack at C-6 of cytosine by a group at the active site of the DNA. Methyltransferase activates C-5 of cytosine as a methyl acceptor by saturating the 5-6 double bond. AdoMet donates a methyl group to C-5 of cytosine to form AdoHcy and the bracketed dihyrocytosine intermediate shown. Dissociation of the enzyme from the complex results in the regeneration of the 5-6 double bond to produce 5-methylcytosine. In the alternate pathway shown below the brackets, the protonated form of the dihydrocytosine intermediate undergoes hydrolytic deamination to generation dihydrothymine (bottom center). Dissociation of the enzyme from this intermediate results in the regeneration of the 5-6 double bond to form thymine.

FIG. 6B: Stable Enzyme-DNA Complex with 5-FC: C-5 of 5-FC, can also be activated as a methyl-acceptor through nucleophilic attack by the DNA methyltransferase at C-6. However, transfer of the methyl-group from AdoMet results in a stable covalent complex between DNA and the enzyme, because neither the C—F nor the C—CH$_3$ bond at C-5 can be broken to regenerate the 5-6 double bond in the cytosine ring.

FIG. 7 depicts mechanism-based labelling of the human DNA(cytosine-5)methyltransferase.

FIG. 7A: As starting material, a 47mer was synthesized from β-cyanoethylphophoramidite precursors using an ABI DNA synthesizer. The 47mer was constructed so as to link a long block of DNA to a shorter complementary block of DNA through a tether consisting of five thymine residues. A 5-methylcytosine residue was introduced during synthesis at position 17 (indicated with m). Molecules of this type form unimolecular foldbacks and are self-priming substrates for DNA polymerase I. In order to generate an oligodeoxynucleotide in which position 48 was occupied by 5FC, 5-FdCTP synthesized by the method of Ruth, et al. Mol. Pharm. 20:415 (1981) was used in place of dCTP during extension with the Klenow fragment of DNA polymerase I, placing 5FC at residues (indicated with F) between positions 48 to 65 normally occupied by C. The FdC residue at position 48 is indicated with an asterisk. Extension to full length was demonstrated by gel electrophoresis on 20% polyacrylamide sequencing gels. The product 65mer was purified by HPLC on a FACS anion exchange column (Waters Associates, Medford, Mass.). The presence of 5-FdC, 5mdC, and other deoxynucleosides in appropriate stoichiometry was demonstrated by HPLC analysis of the nucleoside produced after digestion of the 65mer with nuclease P1 and bacterial alkaline phosphatase using the method of Palmgren, et al. Biochim. Biophys. Acta 1049:293 (1990).

FIG. 7B: Primer extension products were end-labelled using T4-polynucleotide kinase and incubated with a crude DNA methyltransferase preparation under the conditions given below. The product was concentrated by precipitation with trichloroacetic acid and resuspended in buffer containing β-mercaptoethanol and sodium dodecylsulphate. After heating to 95° C. for 5 minutes the sample was separated by electrophoresis through sodium dodecylsulphate containing polyacrylamide gels. $^{32}$P was visualized by autoradiography. Lane 1: 5FdC-65mer+complete reaction mixture: 50 mM4-[2-hydroxyethyl]-1-piperazine-ethanesulfonic acid (pH 7.0) (HEPES), 50 mM NaCl, 2 mM dithiothreitol, 75 μM spermine, 10% (v/v) glycerol, and 6.0 μM [$^3$H-methyl]AdoMet. Lane 2: 5FdC-containing 65mer+reaction mixture lacking AdoMet. Lane 3: dC-containing 65mer+complete reaction mixture.

FIG. 8 depicts chromatographic Analysis of Enzymatically Labelled DNA.

A duplex oligodeoxynucleotide 30mer (inset) was enzymatically methylated in the complete reaction mixture containing [³H-methyl]AdoMet labelled in the methyl-moiety. After digestion of the labelled oligodeoxynucleotide with nuclease P1 and bacterial alkaline phosphatase, the liberated nucleosides were separated by HPLC on a μ bondapack C18 column. (Palmgren et al, *Biochem. Biophys. Acta* 1049:293 (1990)) Fractions we collected and tritium was quantified by scintillation counting. 8(A) Tritium profile. 8(B) Absorbance profile.

Figure 1:
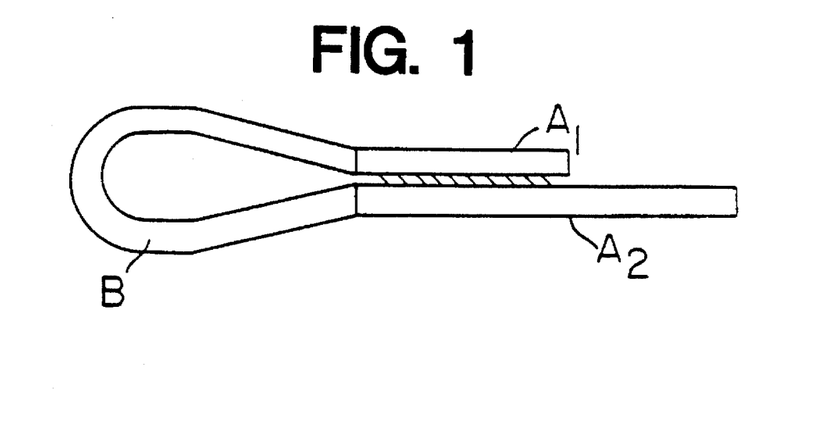
FIG. 1 is a two-dimensional generalized schematic depiction of an HBO in which the $A_1$ and $A_2$ blocks are self-associated.
Figure 2:
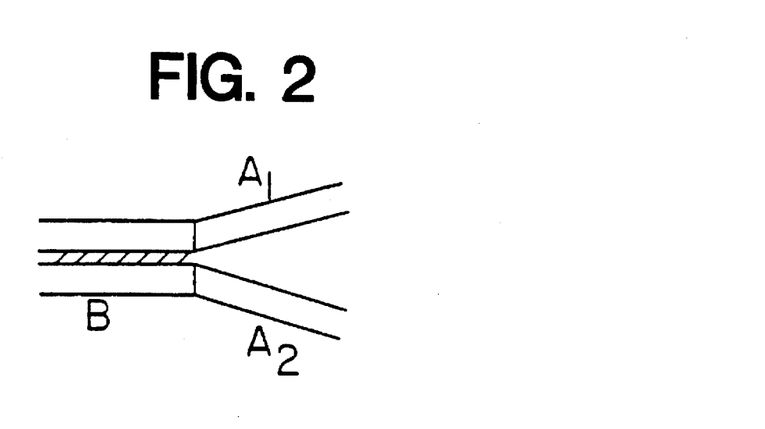
FIG. 2 depicts an HBO in which the linker block B is internally self-associating, e.g., a homologous DNA sequence, flanked by $A_1$ and $A_2$ blocks such as peptides or organic polymers which do not self-associate and which are constrained in juxtaposition by the self-association energy of the linker block. Suitable DNA sequences for the B blocks of such HBOs include a stretch of hydrized nucleotides, generally a sequence of about 15 to 50 bases to provide the self-association energy appropriate to maintain the desired juxtaposition of the $A_1$ and $A_2$ blocks. Suitable peptides for use as A blocks contain from about 5 to about 30 residues. Suitable A block polymers include RNA, DNA, peptides or mixed RNA-DNA polymers having 12 to 150 nucleotides.

Formula I schematically represents one form of an HBO of the kind depicted by FIG. 1:

I.

in which R is an alkyl or aryl group of from about 1 to about 10 carbon atoms and x may be from about 3 to about 12. When x is greater than about 10, these HBO's are surfactive.

The number, n, of B block moieties depends upon the properties desired in the HBO. For many purposes n is from about 5 to about 20.

Appropriate selection of the $A_1$, B and $A_2$ blocks yields bioengineered catalysts in which catalysis is carried out by an appropriately constrained peptide, protein or RNA block. In addition, hydrophobic B blocks, e.g., amino-alkyl phosphonates, amino-aryl phosphonates, yield HBOs which are surfactants, particularly when the self-associating blocks are DNA.

EXEMPLIFICATION OF THE INVENTION

Example I

This example demonstrates the scope and significance of the invention. To do so, it identifies a specific question which has arisen in scientific research, describes the design of an HBO for use in answering the question, exemplifies the synthesis of the postulated HBO and shows that the synthesized HBO functions as intended.

The question addressed concerns the substrate specificity of the human DNA methyltransferase, i.e., whether the enzyme is capable of methylating across a gap in duplex DNA.

A 30 mer and a 13 mer were selected to provide a gapped duplex DNA as depicted by Formula II:

5'GTCCACCAGATCC3' (13 mer) SEQ ID NO:1
3'CAGGTGGTCTAGGCCCGATGGACCGGAGCT5' (30 mer) SEQ ID NO:2

II.

Prior experience indicated that the Formula II molecule might be unstable due to the short region of homology. Stability was achieved by linking the 13 mer and the 30 mer by a block effective to promote the annealing under the conditions contemplated for the reaction, i.e., 37° C., 50 m HEPES, pH7.1, 70 μM Spermine, 1.5 μM 5-adenosyl-L-(methyl-³H) methionine [³H AdoMet].

The design of the linker block raised two questions: (1) what moiety should be used to construct it, and (2) how long should it be? Hydrophobic moieties were rejected to preclude any test of the capability of the enzyme to interact with a detergent.

Cyanoethyl disopropyl phosphoramidite

III.

was chosen as the linker moiety because it is appropriately protected for phosphoramidite synthesis and hence could be added to the termini DNA strands of the Formula II duplex.

Computer modelling in which the desired molecule was constructed in BIOGRAPH was used to select the length of the linker group. Monomeric methane moieties were condensed to the 5' phosphate oxygen of the 13 mer until a methylene chain $(-CH_2-)_n$ long enough to reach the 3' hydroxyl of the 30 mer without producing a conformational change in the Formula I duplex DNA was constructed. The minimum length was determined to be $24(-CH_2-)$moieties. The selected linker monomer is somewhat longer than such moieties. Accordingly, a linker block consisting of five linker units "L" was selected. The HBO to be synthesized is illustrated by Formula IV:

IV.

in which

Oligodeoxynucleotide Preparation and Characterization

Single strand oligodeoxynucleotides were synthesized using the phosphoramidite method (Sinha, N. D., et al., *Nucleic Acids Res.* 12:4539–4557 (1984)). The single stranded products were purified by polyacrylamide gel electrophoresis and high performance liquid chromatography as described by Tan, et al., Cold Spring Harbor Symp. on Quantitative Biology XLVII 383–391 (1982). The sequence of each of the oligodeoxynucleotides was verified using the method of Maxam and Gilbert.

Duplex Oligodeoxynucleotides

The HBO was synthesized in a manner similar to the standard production of oligodeoxynucleotides. The amino group is protected by a monomethoxyl trityl MMT or dimethoryl trityl DMT group and the phosphate group is simultaneously activated. After the MMT or DMT group was removed, the amino group was neutralized after each addition so that the next monomer could be added.

Formula V schematically depicts the HBO produced by this example:

The HBO product of this example is an excellent substrate for human DNA methyltransferase as evidenced by the following test which is dependent on the spatial conformation of the molecule.

DNA (cytosine-5)methyltransferase was purified from human placentas as described in Smith, supra. When stored under the conditions described there, the enzyme loses less than 50% of its activity per year at −70° C. Two sets of assay conditions were employed. The unit of enzyme activity is defined in terms of the assay conditions used during enzyme purification with heat-denatured *Micrococcus lysodeikticus* DNA substrate (Smith supra). A unit of enzyme activity is the amount redquired to catalyze the incorporation of 1 pmole of methyl groups into TCA insoluble DNA in one hour at 37° C. under those conditions.

For the determination of initial velocities with oligodeoxynucleotide substrates, the enzyme was dialyzed for 3 hours in a Hoefer microdialyzer (Health Products Inc., Rockford, Ill.) against 38 mM glycine, 17% v/v glycerol, 5 mM Tris, 10 mM β-mercaptoethanol, pH 7.8 at 4° C. The final reaction volume of 100 μl contained: 0.4 μg total DNA, 50 mM HEPES pH 7.0, 50 mM NaCl, 2 mM DTT, 75 μM Spermine, 10% v/v glycerol and 6.0 mM [$^3$H]AdoMet (Amersham, 15 Ci/mmole). Reaction mixtures were preincubated at 37° C. for 15 minutes before the addition of 44 U of DNA methyltransferase to initiate the reaction. The reaction rate was linear under these conditions for 30 minutes. After 20 minutes of incubation, the reactions were stopped by the addition of 5 ml of cold TCA (5% w/v TCA containing 5 mM potassium pyrophosphate). Tritium incorporated into TCA insoluble DNA was determined as previously described (Smith, S. S., supra).

After enzymatic methylation of the substrate molecules with [$^3$H]5-adenosyl methionine as methyl donor, the labelled duplexes were cleaved with restriction endonucleases MboI and MspI. The products were electrophoretically separated and $^3$H labelled DNA fragments were detected by fluorescence enhanced autoradiography as previously described in Smith, et al. The HBO molecule is refractory to digestion by MspI, consistent with the fact that the looped molecule cannot generate a complete duplex MspI site. On the other hand the same molecule is cleaved by MboI to about 70% completion. The cleavage product is only slightly shorter than the uncut molecule suggesting that MboI cleavage occurs on the cut site on the unmethylated portion of the molecule to produce a molecule that is six nucleotides shorter (on the 3' end) than the parent molecule. This partial cleavage pattern could be produced by the presence of the linkers in the loop, or it could mean that the fold-back structure does not form in a way that provides the enzyme with a completely recognizable cleavage site.

In any event, the DNA methyltransferase recognizes the structure and actively methylates it. The data given in Table I shows that the presence of a methyl group at the end of the short arm of the loop stimulates the reaction more than 100 fold (48L-1), while the presence of the methyl group at position 17 (bases numbered from the 5' end of the molecule) (48L-2) does not stimulate the reaction rate.

Figure 4:
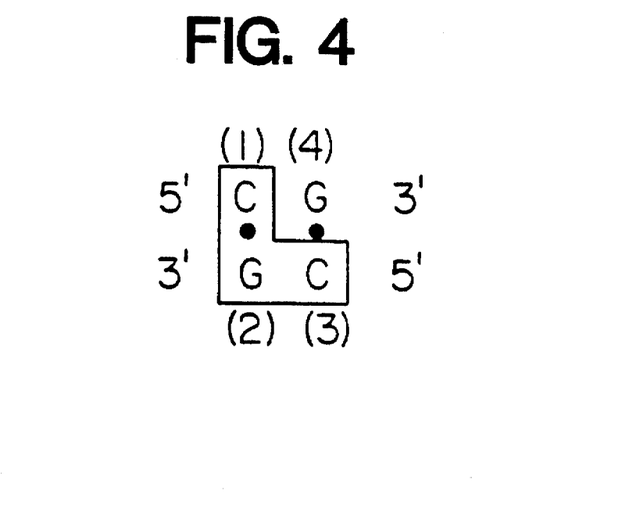
FIG. 4 illustrates a three nucleotide rule for DNA methylation with DNA methyl transferase.

These findings are consistent with a three nucleotide rule for DNA methylation which may be elucidated by reference to FIG. 4. Referring to the figure, if enzymatic methylation occurs at cytosine (3), only the nucleotides shown in the L-shaped box are required. The enzyme must interact with cytosine (1) and its hydrogen bonded guanine (2) as it methylates cytosine (3). Guanine (4) is not required and can in fact be missing, alkylated, or replaced with any base. Even when the structure of a DNA substrate is not well understood, the application of this "L-Test for Methylation" or "3 nucleotide rule" is useful in predicting the methylation pattern applied in vitro.

TABLE I

| Molecule Code | Structure | DNA Methyltransferase Substrate Activity (FMOLE/MIN) |
|---|---|---|
| 48L-1 | L—L<br>/    \         M<br>L      GTCCACCAGATC C3©<br>\|<br>L      CAGGTGGTCTAGGCCCGA' GGACCGGAGCT5©<br>\   /<br> L | SEQ ID NO:1<br>SEQ ID NO:2<br>157 |
| 48L-2 | L—L<br>/    \<br>L      GTCCACCAGATCC3 ©<br>\|<br>L      CAGGTGGTCTAGGCCCGATGGACCGGAGCT5©<br>\   /            M<br> L | SEQ ID NO:1<br>SEQ ID NO:2<br>11 |
| 48L-3 | L—L<br>/    \<br>L      GTCCACCAGATCC3'<br>\|<br>L      CAGGTGGTCTAGGCCCGATGGACCGGAGCT5'<br>\   /<br> L | SEQ ID NO:1<br>SEQ ID NO:2<br>12 |

Figure 3:
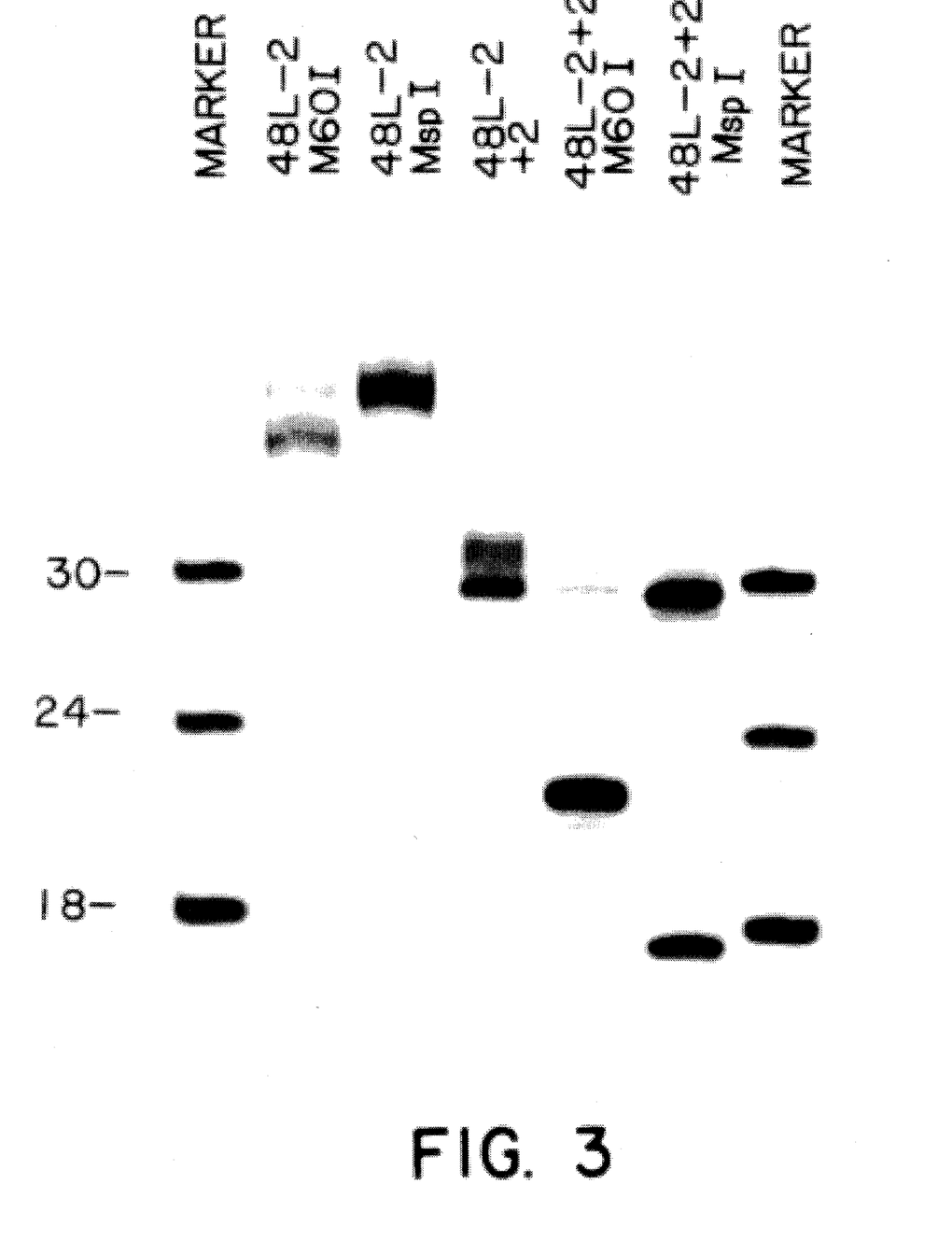
FIG. 3 is a copy of an autoradiograph illustrating the utility of an HBO as a human methyl transferase substrate.

Enzymatic methylation of the HBO 48L-2 is demonstrated by the strong tritium signal in lanes 2 and 3 of the FIG. 3 autoradiograph. To produce the autoradiograph HBO 48L-2 was exposed to human DNA methyltransferase in the presence of S adenosyl methionine as the methyl group donor. The reaction product was separated by polyacrylamide gel electrophoresis and the presence of enzymatically tritiated DNA was demonstrated by fluorescence enhanced autoradiography. Referring to FIG. 3, lanes 1 and 7 include markers corresponding to 18, 24 and 30 bases. MboI and MspI identify restriction enzymes.

HBO's of all types may be synthesized by techniques known to the skilled person. Linker blocks B may be added to pre-self associated $A_1$ and $A_2$ blocks as typified by the example. Alternatively, all of the blocks may be separately synthesized and the desired HBO constructed from these prefabricated blocks. Such a procedure is preferred for the production of HBO's which involve the linkage of peptide and DNA blocks.

Example II

Example II illustrates one method for producing an HBO of schematic formula (DNA-2)-peptide-(DNA-1).

Synthesis of DNA-1

An amino alcohol is reacted with one equivalent of monomethoxytrityl chloride (MMT-Cl) in pyridine. The MMT-amino alkanol product is purified by chromatography and then reacted with an appropriate phosphitylating agent forming a cyanoethyldiisopropylamino phosphite or a hydrogen phosphonate reagent or any other phosphite reagent known to the skilled worker. The product of this reaction is an activated phosphite reagent useful in any standard DNA synthesis machine. These reactions are illustrated by the following equation:

This activated phosphate reagent is coupled to the 5'OH of a growing DNA molecule synthesized in known manner on a solid support such as controlled pore glass (CPG). The MMT group is then removed with dichloroacetic acid or trichloroacetic acid and the amino group is neutralized to permit coupling to the next incoming phosphite reagent. Neutralization is accomplished by treating the growing DNA molecule with a dilute basic solution such as 1% triethyl amine in acetonitrile for a few seconds to convert the protonated amino group into a free amino group. These reactions are illustrated by the following equations:

Synthesis of Peptide DNA-1

A peptide having a free amino and a free carboxyl group is coupled to DNA-1 in known manner, e.g., by use of a water soluble carbodiimide as illustrated by the following equation:

Synthesis of DNA-2

A DNA fragment with a free carboxylic acid on the 3' end is synthesized on a solid support, for example, by connecting a DMT protected hydroxy carboxylic acid such as the DMT protected 6-hydroxyhexanoic acid to an amino-propyl CPG using a carbodiimide. After the coupling, the DMT group is removed in known manner using dichloroacetic acid in dichloromethane. A second reaction with a DMT protected hydroxy carboxylic acid is completed. The DMT group is again removed and again coupled with the DMT-protected 6-hydroxyhexanoic acid using a carbodiimide and dimethylaminopyridine to provide controlled pore glass as a support for the synthesis of DNA-2 in known manner. These reactions are illustrated by the following equations:

Synthesis of (DNA-2)-Peptide-(DNA-1)

After the synthesis is completed, the DNA-2 is deprotected in the standard way yielding a 5' DMT-DNA-2. The 3' carboxyl of this molecule is coupled to the amino group of the peptide-DNA-1 and the DMT group is removed to yield as the final product DNA-2-peptide-DNA-1.

Example III

Example III illustrates the preparation of an oligonucleotide containing 5FC residues. This oligonucleotide is shown to be a mechanism based inhibitor of DNA methyl transferase.

Figure 5A:
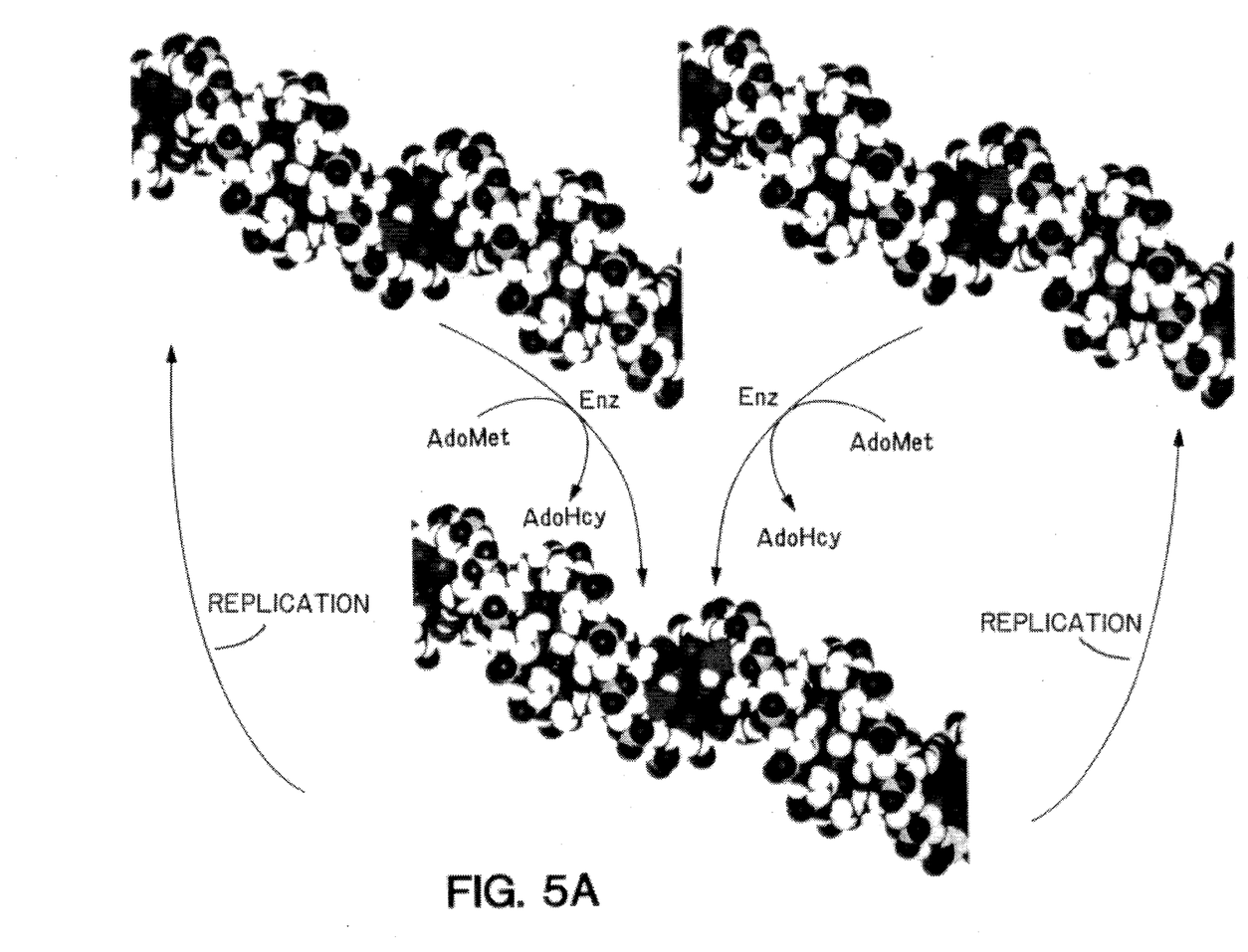
FIG. 5A: Space-filling models of the asymmetrically methylated B-DNA molecule and the symmetrically methylated B-DNA molecule produced by the enzyme, depict the reaction. Methyl groups on 5-methylcytosine residues at the CG dinucleotide pair are shown.

As shown by FIG. 5A, methylated pyrimidines are generated from the dihydropyrimidine intermediates by elimination of the hydrogen atom at C5 and the enzyme moiety at C6 to regenerate the 5-6 double bond. This should not be possible when the pyrimidine being attacked is 5FC, because the enzyme cannot break the F—C bond. For this reason, nucleophilic attack and methyl-group transfer at a 5FC residue will produce a stable complex between DNA and the enzyme (FIG. 5B).

Figure 5B:
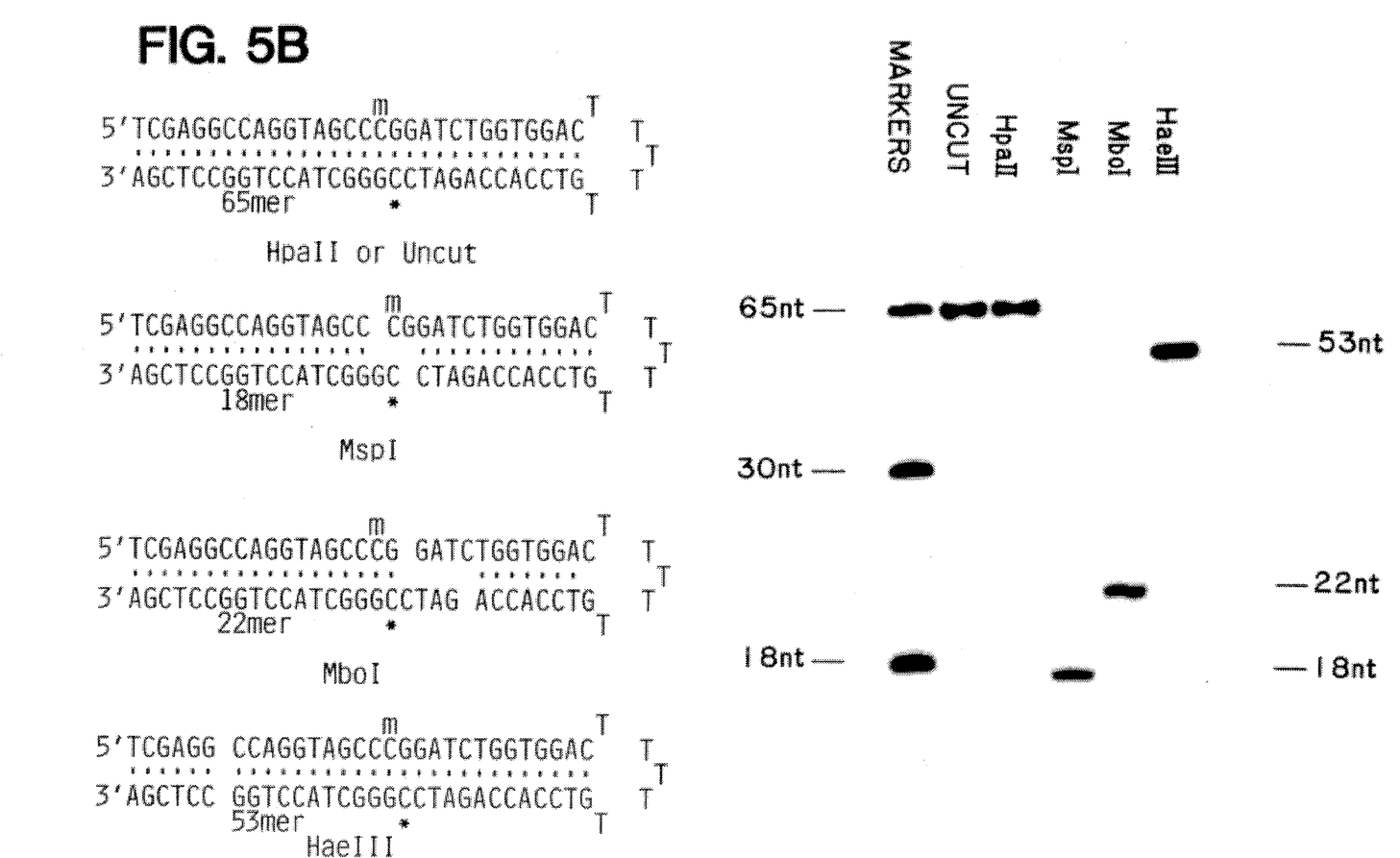
Figure 7A:
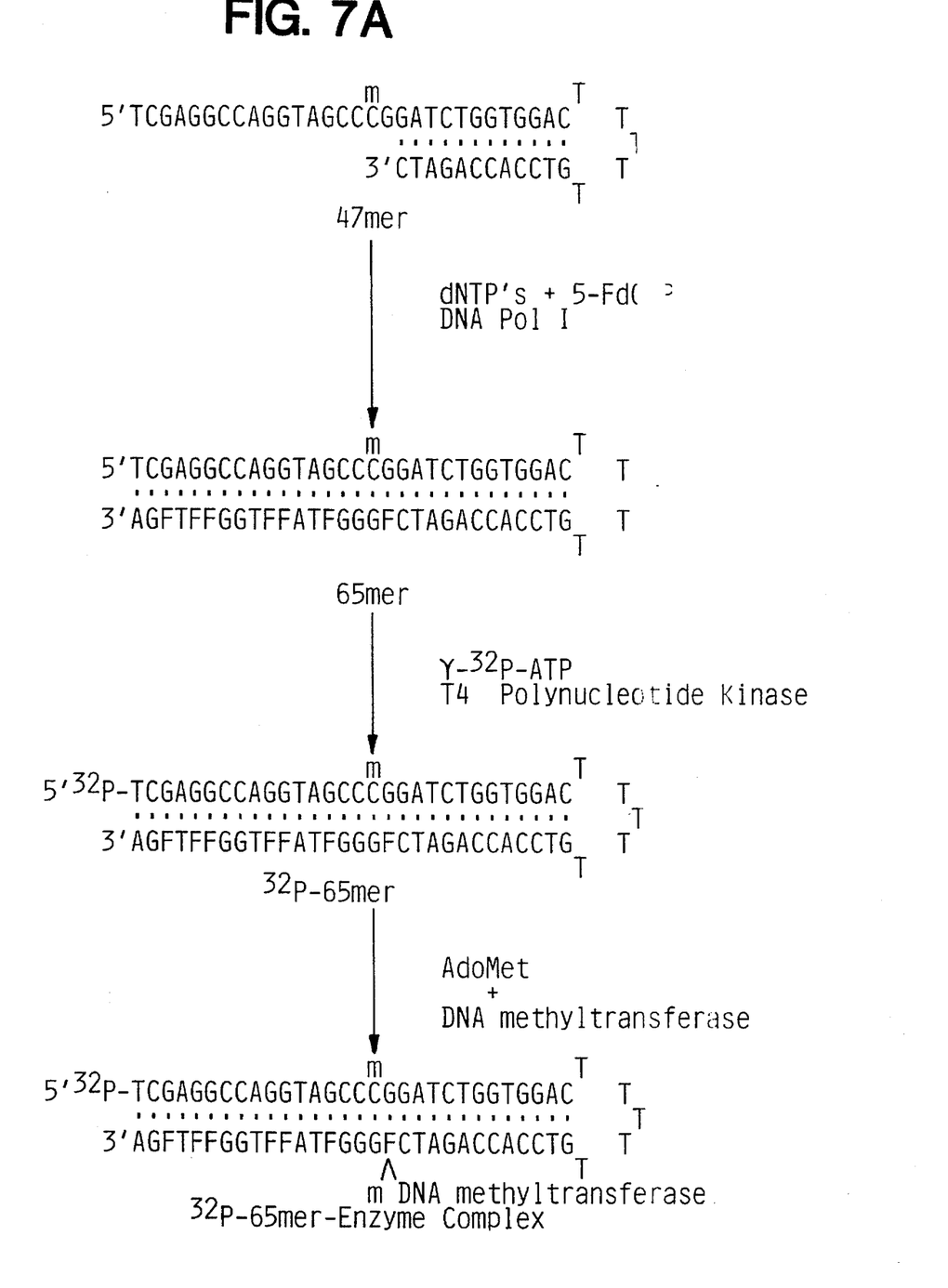

To detect the putative intermediate, the enzymatic methylation of the asymmetrically methylated foldback depicted in FIG. 5B was studied. Restriction analysis of the enzymatically tritiated product using previously established methods (see, Smith, et al., *J. Mol. Biol.* 217:39 (1991)) showed that the 5-methylcytosine residue at position 17 directed the enzyme to methylate the cytosine residue located at the symmetrically placed site in the CG dinucleotide pair (position 48). A rate enhancement of about 100 fold over the rate observed with the unmethylated foldback was coupled with a very strong specificity for the cytosine at position 48 (FIG. 5B). This specificity was then exploited by producing an oligodeoxynucleotide containing 5FC at position 48. To do this, DNA polymerase I was used to extend a self-priming 47mer in the presence of 5FdCTP as shown in FIG. 7A.

Figure 7B:
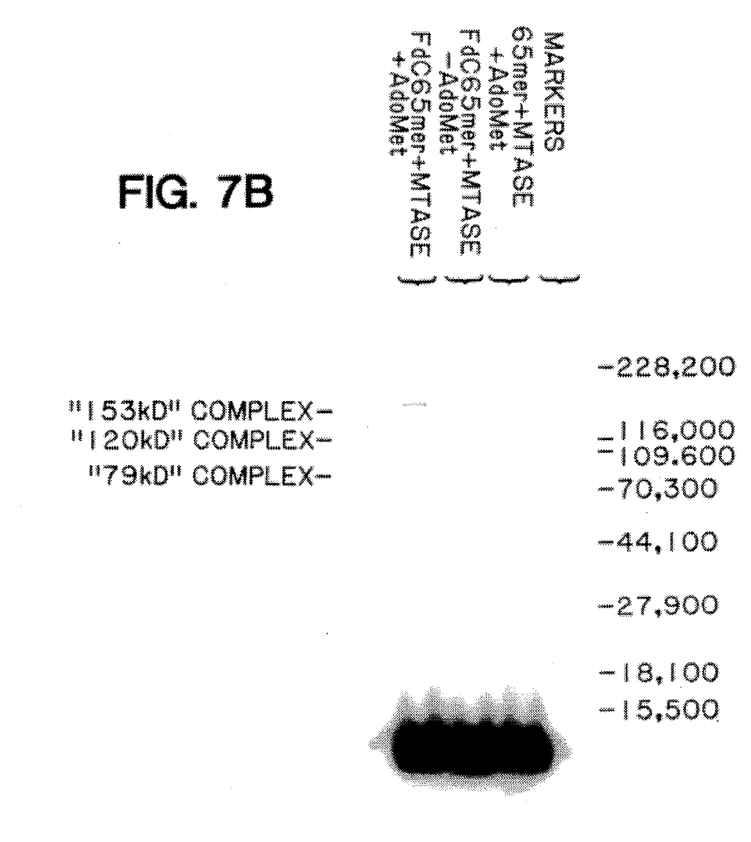
Figure 7C:
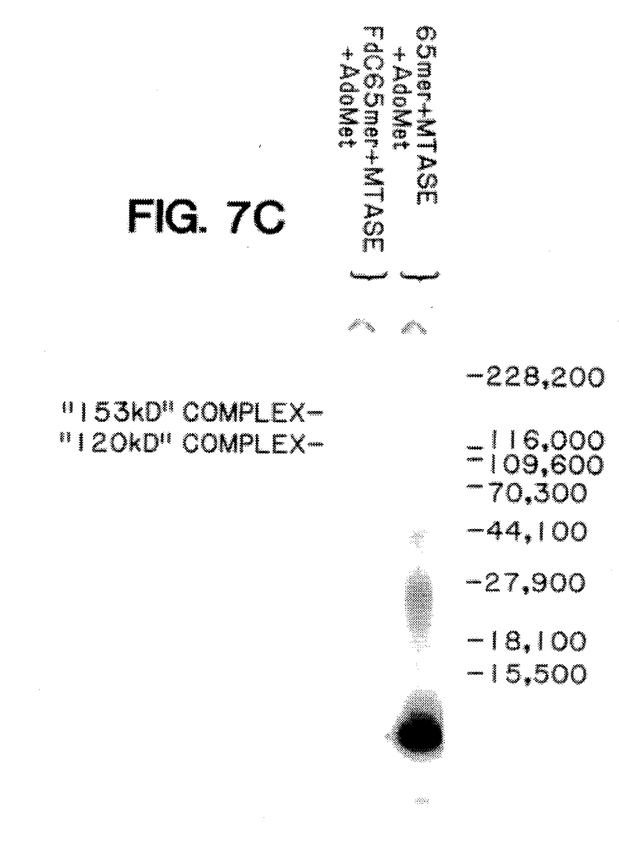
FIG. 7C: Unlabelled primer extension products were incubated with the methyltransferase preparation and separated by electrophoresis through sodium dodecyl sulphate-polyacrylamide gels as in A except that the tritiated methyl-groups applied to the foldback were visualized by fluorography after impregnating the gels with En$^3$Hance. See, Smith, et al., J. Mol. Biol. 217:39 (1991). Lane 1: complete reaction mixture+5FdC-containing 65mer. Lane 2: Complete reaction mixture+dC-containing 65mer.
Figure 8A:
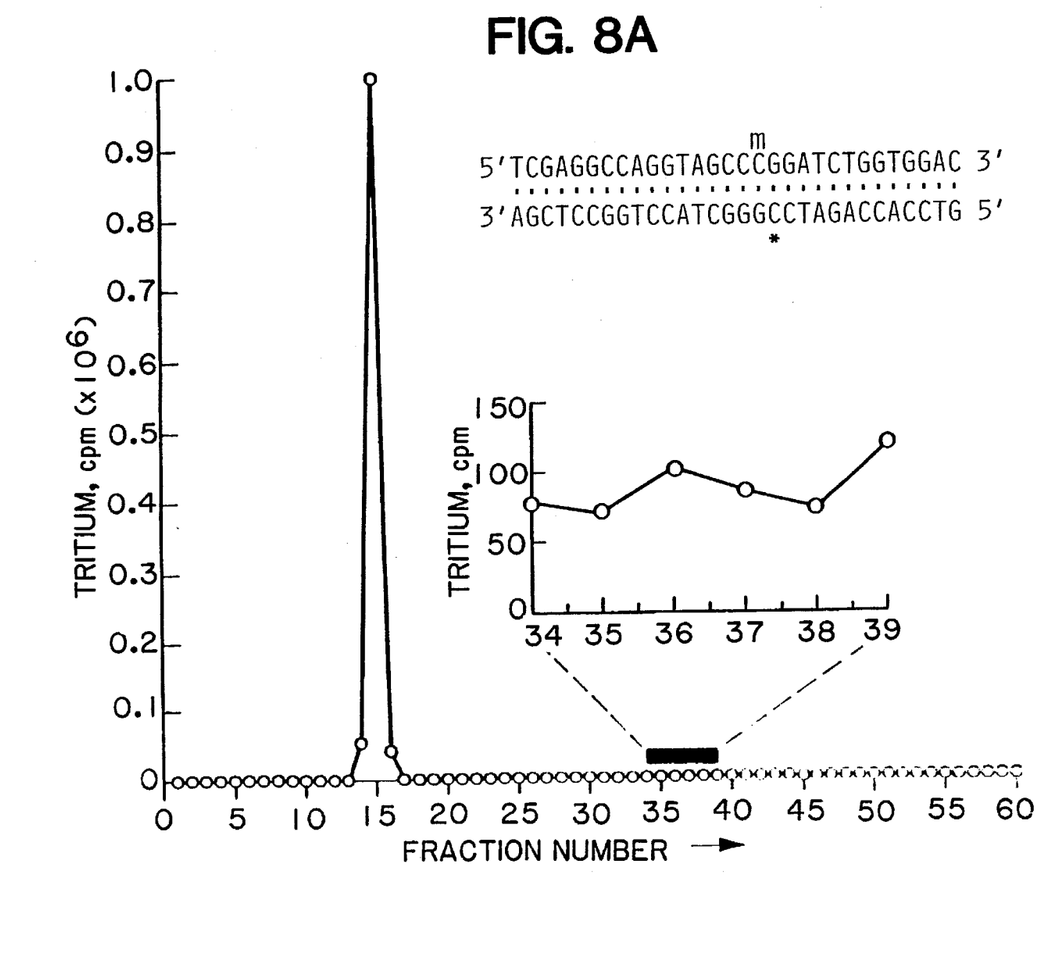
Figure 8B:
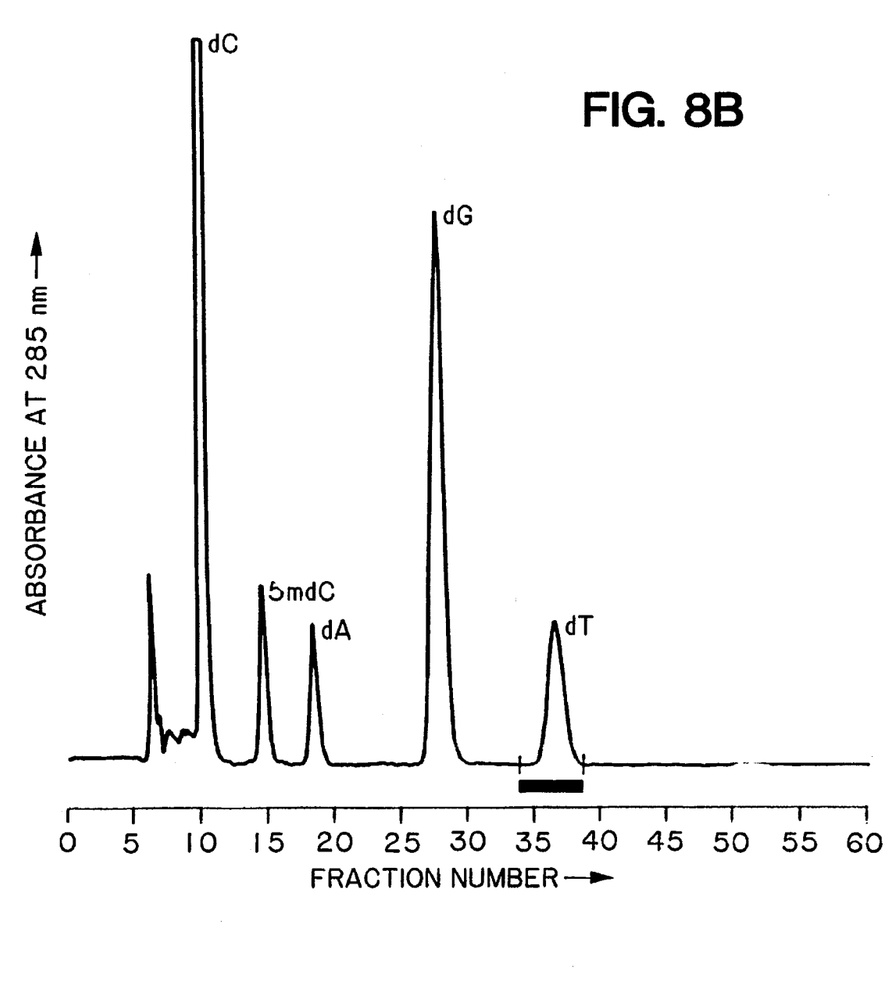

When the $^{32}$P end-labelled oligodeoxynucleotide was incubated with partially purified DNA methyltransferase and S-adenosylmethionine (AdoMet) covalent complexes could be detected as slow moving bands in sodium dodecylsulfate (SDS) polyacrylamide gels. The complexes survived 5 minutes at 95° C. in SDS and the reducing agent β-mercaptoethanol (FIGS. 7B and 7C). The major complex had an apparent molecular weight of 160 kD, which is consistent with a complex formed between the 24 kD oligodeoxynucleotide and the 126 kD catalytic unit obtained in homogeneous form by further purification. See, Zucker, et al., *J. Cell. Biochem.* 29:337 (1985). The complexes with apparent molecular weights of 130 kD and 90 kD could correspond to the 105 kD and 79 kD forms of the placental enzyme seen in immunoprecipitation experiments. See, Pfeiffer, et al., *J. Biol. Chem.* 260:13787 (1985). Complexes were not formed in the absence of AdoMet suggesting that the transfer of a methyl group to DNA was required for their formation. The complexes were not observed with a control oligodeoxynucleotide prepared by primer extension with dCTP in place of 5FdCTP. Tritium fluorography could also be used to visualize the complexes when methyl groups were transferred to DNA by the enzyme from [$^3$H-methyl]AdoMet (FIG. 7C). When the 5FC containing oligodeoxynucleotide was used, more than 80% of the label was observed in complexes. The small amount of label at the position of the oligodeoxynucleotide 65mer could be attributed to nonspecific breakdown of the complex. When the oligodeoxynucleotide 65mer lacking 5FC was incubated with the enzyme and [$^3$H-methyl]AdoMet, no label was observed in complexes. The bulk of the tritium label was observed at the position of the 65mer. Based on the specific activity of the homogeneous enzyme, about 20% of the available DNA methyltransferase was converted into stable complexes in 30 minutes with the 5FC containing oligodeoxynucleotide. Incorporation into trichloracetic acid insoluble material was about 40-fold lower when 5FC was present in the oligodeoxynucleotide than when it was absent, indicating that the reaction with the 5FC-containing oligodeoxynucleotide was stoichiometric while that with the oligodeoxynucleotide lacking 5FC was catalytic. More specifically, 9800 cpm/pmole tritiated methyl groups, when AdoMet is spotted directly onto a glass fiber filter and counted in scintillation fluid, is observed. The specific activity of homogeneous enzyme is about 40,000 U/mg, its molecular weight is about 126 kD. When 5.7 U of enzyme (143 ng) was incubated with an excess of 5FC-containing DNA, 2,212 cpm $^3$H was incorporated into trichloracetic acid insoluble material. If it is assumed that one mole of substrate bound per mole of enzyme, this implies that (2,212 cpm/9800 cpm/pmole) (126000 pg/pmole)=28.4 ng of enzyme is contained in the complex, for an efficiency of about 20% (28.4/143).

Figure 6A:
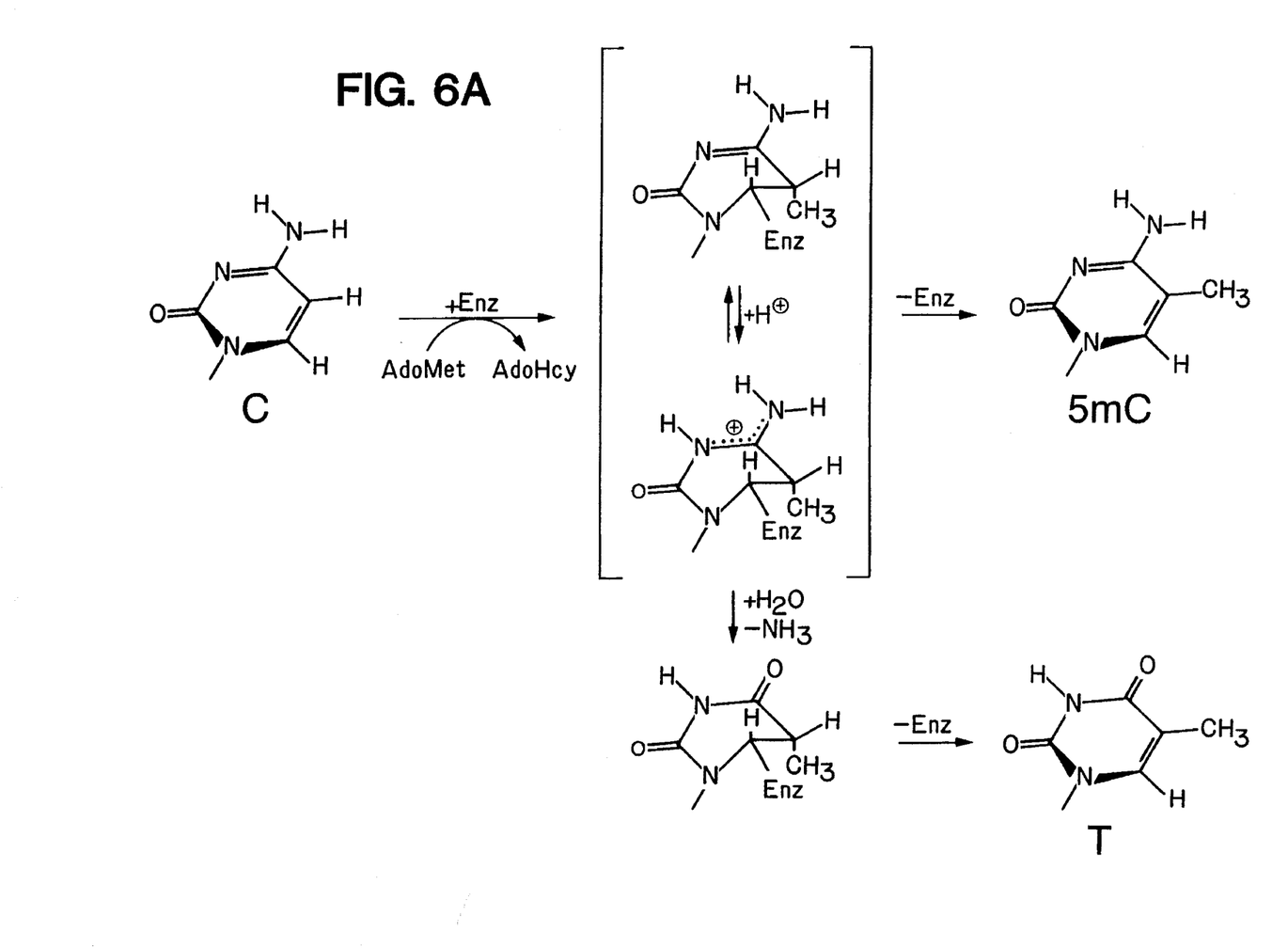
Figure 6B:
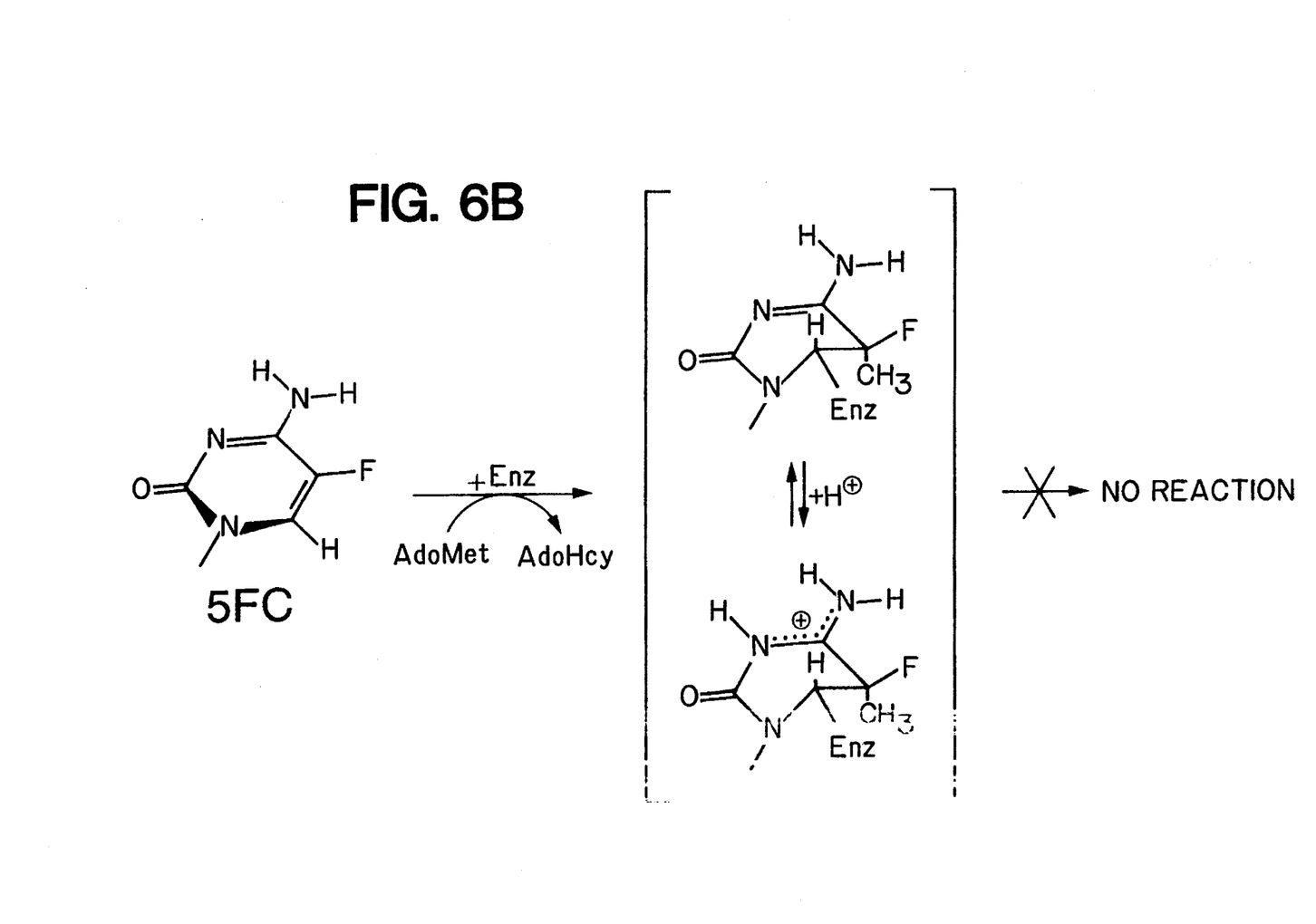

The data described above indicates that the enzyme operates via the mechanism described in FIG. 6. Several of the consequences drawn based on the assumption of the formation of this intermediate by eukayrotic methyltransferases have been discussed. See, Smith, et al. *J. Mol. Biol.* 217:39 (1991) and Santi, et al. *Cell* 33:9 (1983). The potential for hydrolytic deamination during catalysis has not yet been explored however. It has sometimes been noted that MspI digests like that shown in FIG. 5 exhibit a small residue of enzymatically methylated DNA that is uncleaved. Since the G/T mispair that would be generated by hydrolytic deamination as described in FIG. 6A would block MspI cleavage, possibility that a low level of deamination might occur during enzymatic methylation was investigated. After enzymatic labelling, the tritium-labelled oligodeoxynucleotide was digested to deoxynucleosides and the digest was analyzed by HPLC. A comparison of the tritium profile and the absorbance profile in FIG. 5 shows that tritium-labelled methyl groups were detected in 5-methyldeoxycytidine but not in thymidine. Assuming that the limit of detection is about 50% above background, calculation shows that less than 1 thymidine would be produced for every 20,811 cytosine residues methylated. More specifically, the average cpm for the 5-methylcytosine peak was 9.78×10$^5$. Average background in the region of thymidine peak was 93 cpm. Assuming a detection limit of 50% above background: 9.78×10$^5$/47=20,811. This means in vitro fidelity observed with the human DNA methyltransferase in copying a methylation pattern would be comparable to the fidelity (1/2930 to 1/47,500) observed for mammalian polymerases in copying a DNA sequence. See, Loeb, et al. *Ann. Rev. Biochem.* 52:429 (1982). Since there is no apparent reason to suspect from the data that thymidine residues were actually produced during the reaction, the fidelity of the methyltransferase may in fact be considerably better than that of the mammalian polymerases.

---

We claim:

1. A method for predicting an in vitro methylation pattern of a double stranded DNA molecule, said method comprising (i) determining the nucleotide sequence of said DNA molecule, and (ii) determining whether the sequence determined in step (i) includes a site as depicted by FIG. 4 wherein the presence of said site in said sequence indicates that an in vitro methylation of said sequence is likely to occur thereat.

2. A method for predicting an in vitro methylation pattern of an oligodeoxynucleotide, said method comprising (i) determining the nucleotide sequence of said oligodeoxynucleotide, and (ii) determining whether the sequence determined in step (i) includes a site as depicted by FIG. 4 wherein the presence of said site in said sequence indicates an in vitro methylation of said sequence is likely to occur thereat.

3. A method for predicting an in vitro methylation pattern of an oligodeoxynucleotide, said method comprising (i) determining the nucleotide sequence of said oligodeoxynucleotide, and (ii) determining whether the sequence determined in step (i) includes a three nucleotide motif as depicted by FIG. 4 wherein the presence of said motif in said sequence indicates an in vitro methylation of said sequence is likely to occur thereat.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 13
        ( B ) TYPE: Nucleotide
        ( C ) STRANDEDNESS: Single (D) TOPOLOGY: Unknown (xi) SEQUENCE DESCRIPTION: SEQ ID NO: 1:

GTCCACCAGA TCC                                                            13

(2) INFORMATION FOR SEQ ID NO: 2:

(i) SEQUENCE CHARACTERISTICS:
(A) LENGTH: 30
(B) TYPE: Nucleotide
(C) STRANDEDNESS: Single
(D) TOPOLOGY: Unknown (xi) SEQUENCE DESCRIPTION: SEQ ID NO: 2:

CAGGTGGTCT AGGCCCGATG GACCGGAGCT                                          30

(2) INFORMATION FOR SEQ ID NO: 3:

(i) SEQUENCE CHARACTERISTICS:
(A) LENGTH: 30
(B) TYPE: Nucleotide
(C) STRANDEDNESS: Single
(D) TOPOLOGY: Unknown (xi) SEQUENCE DESCRIPTION: SEQ ID NO: 3:

TCGAGGCCAG GTAGCCCGGA TCTGGTGGAC                                          30

(2) INFORMATION FOR SEQ ID NO: 4:

(i) SEQUENCE CHARACTERISTICS:
(A) LENGTH: 30
(B) TYPE: Nucleotide
(C) STRANDEDNESS: Single
(D) TOPOLOGY: Unknown (xi) SEQUENCE DESCRIPTION: SEQ ID NO: 4:

AGCTCCGGTC CATCGGGCCT AGACCACCTG                                          30

(2) INFORMATION FOR SEQ ID NO: 5:

(i) SEQUENCE CHARACTERISTICS:
(A) LENGTH: 12
(B) TYPE: Nucleotide
(C) STRANDEDNESS: Single
(D) TOPOLOGY: Unknown (xi) SEQUENCE DESCRIPTION: SEQ ID NO: 5:

CTAGACCACC TG                                                             12

(2) INFORMATION FOR SEQ ID NO: 6:

(i) SEQUENCE CHARACTERISTICS:
(A) LENGTH: 30
(B) TYPE: Nucleotide
(C) STRANDEDNESS: Single
(D) TOPOLOGY: Unknown (xi) SEQUENCE DESCRIPTION: SEQ ID NO: 6:

AGNTNNGGTN NATNGGGNCT AGACCACCTG                                          30